United States Patent
Stone et al.

(12) 
(10) Patent No.: US 10,952,687 B2
(45) Date of Patent: Mar. 23, 2021

(54) CATHETER DETECTION, TRACKING AND VIRTUAL IMAGE RECONSTRUCTION

(71) Applicant: University of Rochester, Rochester, NY (US)

(72) Inventors: Jonathan Jay Stone, Rochester, NY (US); Brenton Joseph LaRiccia, Farmington, NY (US)

(73) Assignee: University of Rochester, Rochester, NY (US)

( * ) Notice: Subject to any disclaimer, the term of this patent is extended or adjusted under 35 U.S.C. 154(b) by 1299 days.

(21) Appl. No.: 15/062,061

(22) Filed: Mar. 5, 2016

(65) Prior Publication Data

US 2016/0256120 A1    Sep. 8, 2016

Related U.S. Application Data

(60) Provisional application No. 62/129,254, filed on Mar. 6, 2015.

(51) Int. Cl.
| | |
|---|---|
| *A61B 6/12* | (2006.01) |
| *A61B 6/00* | (2006.01) |
| *A61M 25/01* | (2006.01) |
| *A61B 90/94* | (2016.01) |
| *A61B 17/12* | (2006.01) |
| *A61B 90/00* | (2016.01) |
| *A61B 34/20* | (2016.01) |

(52) U.S. Cl.
CPC ............... *A61B 6/12* (2013.01); *A61B 6/485* (2013.01); *A61B 6/501* (2013.01); *A61B 6/5205* (2013.01); *A61B 17/1214* (2013.01); *A61B 17/12113* (2013.01); *A61B 90/94* (2016.02); *A61M 25/0108* (2013.01); *A61B 2017/1205* (2013.01); *A61B 2034/2048* (2016.02); *A61B 2090/067* (2016.02); *A61B 2090/364* (2016.02); *A61B 2090/376* (2016.02); *A61B 2090/3966* (2016.02)

(58) Field of Classification Search
CPC .......... A61B 17/12113; A61B 17/1214; A61B 2017/1205; A61B 2034/251; A61B 2090/067; A61B 2090/364; A61B 2090/376; A61B 2090/3966; A61B 6/12; A61B 6/485; A61B 6/501; A61B 5/5205; A61B 90/94; A61M 25/0108
See application file for complete search history.

(56) References Cited

U.S. PATENT DOCUMENTS

| | | | | |
|---|---|---|---|---|
| 5,944,712 A | * | 8/1999 | Frassica ................ | A61M 25/00 600/434 |
| 6,493,575 B1 | * | 12/2002 | Kesten .................. | A61B 90/36 600/431 |
| 2007/0004981 A1 | * | 1/2007 | Boese ............... | A61M 25/0108 600/433 |

* cited by examiner

*Primary Examiner* — Amelie R Davis
(74) *Attorney, Agent, or Firm* — Patent Technologies, LLC; Robert D. Gunderman, Jr.

(57) ABSTRACT

A catheter and related X-ray imaging system for detection, tracking, and virtual image reconstruction is disclosed. The catheter and imaging system allow for the visualization of the catheter or a part of the catheter such as the tip during procedures that would otherwise obscure the catheter or part of the catheter from view. An example of such a procedure is the deployment of a coil in an aneurysm where the radiodense nature of many coil materials would otherwise make detection and tracking of the catheter tip difficult or impossible. The catheter has detectable markers that provide information to an imaging system regarding the coordinates of the catheter or catheter tip and the direction of the catheter tip during clinical procedures.

10 Claims, 7 Drawing Sheets

CATHETER DETECTION, TRACKING AND VIRTUAL IMAGE RECONSTRUCTION

CROSS REFERENCE TO RELATED PATENT APPLICATIONS

This application claims priority to U.S. Patent Application Ser. No. 62/129,254 filed Mar. 6, 2015 entitled "Catheter Detection, Tracking And Virtual Image Reconstruction" by Jonathan Jay Stone and Brenton Joseph LaRiccia, the entire disclosure of which is incorporated herein by reference.

BACKGROUND OF THE INVENTION

1. Field of the Invention

The present invention relates generally to medical imaging, and more particularly to catheter detection tracking, and virtual image reconstruction.

2. Description of the Related Art

During various angiographic procedures, such as embolization, where a radiodense coil mass is extruded into an aneurysm by way of a catheter, it becomes difficult to image the tip of the catheter with the dark background image of the radiodense coil mass that is being deployed into the aneurysm. The correct movement and placement of the catheter during embolization is critical for not only optimal aneurysm filling, but also for the overall safety of the procedure. Any ambiguities in the position and movement of the catheter tip during procedures such as embolization or stenting represents the potential for error and resulting patient morbidity.

What is therefore needed is an endovascular catheter that can be detected and tracked in real time through the reconstruction of a virtual image of the catheter despite background radio density. What is further needed is an X-ray apparatus and imaging system that can detect markers on the catheter that are in turn translated to position coordinates and overlaid with an image or series of images from the X-ray apparatus where the translated position coordinates also provide trajectory information as the catheter is being placed.

BRIEF SUMMARY OF THE INVENTION

In accordance with the present invention, there is provided a catheter and related imaging system for detection, tracking, and virtual image reconstruction comprising a catheter body having a proximal end and a distal end; a first detectable marker located at the distal end of the catheter body; a second detectable marker located adjacent the first detectable marker; and a quantifiable angular displacement coordinate comprising a locus of points between the first detectable marker and the second detectable marker.

The foregoing paragraph has been provided by way of introduction, and is not intended to limit the scope of the invention as described by tins specification, claims and the attached drawings.

BRIEF DESCRIPTION OF THE DRAWINGS

The invention will be described by reference to the following drawings, in which like numerals refer to like elements, and in which.

Figure 1:
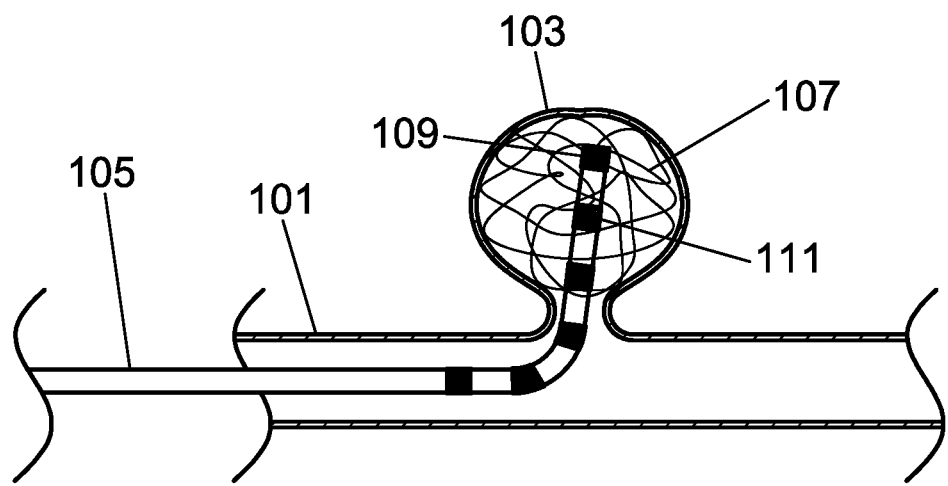
FIG. 1 depicts a first embodiment of the present invention in use.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention, as defined by this specification, claims and drawings attached hereto.

DESCRIPTION OF THE PREFERRED EMBODIMENTS

Described herein is a catheter that provides for detection, tracking, and virtual image reconstruction of an image of the catheter during angiography or similar fluoroscopic procedures, as well as methods and systems to allow for such detection, tracking, and virtual image reconstruction where the image of the catheter would otherwise be obscured by a radiodense object such as a coil, a stent, or the like. The distal end of the catheter comprises a material in a specific pattern that can be identified during angiography. The material may be a radiodense material such as a metal, quantum dots, gamma refraction patterns, gamma emitters, or the like.

Ideally, the novel catheter of the present invention can be used with current fluoroscopic machines. One way to achieve this is by way of a specialized metallic (or other radiodense/reflective) pattern printed, overlaid, or otherwise placed onto the catheter tip. An example of such a material is barium. In addition, in some embodiments of the present invention, the pattern comprises nano-etchings or other nanostructured patterns that provide a unique X-ray signature or scatter. This in turn creates a specialized pattern onto a detector Charge Coupled Device (CCD), and using software that recognizes the special pattern on the catheter, the software can in turn partially reconstruct the catheter's appearance in the proper location. Based on the known distance of the markers, the computer program software can determine magnification and calculate exact size. This would allow for the use of current x-ray detectors already in use. The computer can then reconstruct the catheter despite radiodense materials in close proximity to the catheter.

The markers comprise, for example, a radiodense material to provide a fluoroscopic representation of a trajectory of the catheter during a medical procedure.

Other materials that can be used for the novel markers of the present invention are quantum dots. Quantum dots are an excitable substance that can be "painted" or otherwise coated or applied onto the tip of a distal catheter. The quantum dots absorb one wavelength of light and emit a different wavelength of light, allowing for the release of a specific electromagnetic signal or signature. This coating of quantum dots would ideally absorb gamma radiation and release a slightly modified form of gamma radiation that x-ray detectors and software can identify and mark as being the marker of interest. Alternatively, the detector and/or signal emitter may be a separate unit that is in turn connected to biplane x-ray imaging.

In some embodiments of the present invention, the catheter markers contain a source of electromagnetic radiation that may require a power source and can be detected during angiography and overlaid with vascular imaging. Markers may, in some embodiments of the present invention, have their own source of power, and may be radioactive or otherwise contain a source of radiation that can be detected during fluoroscopic or other X-ray procedures. The markers thus may provide a unique signature in the presence of X-rays to provide a fluoroscopic representation of a trajectory of the catheter during a medical procedure.

The catheter for detection, tracking, and virtual image reconstruction comprises a catheter body having a proximal end and a distal end as seen in the accompanying Figures. There is a first detectable marker located at the distal end of the catheter body and a second detectable marker located adjacent the first detectable marker. There may be additional detectable markers along the tip or body of the catheter to provide for imaging and visualization of the catheter and/or catheter tip near radiodense material that would otherwise obscure the catheter and/or catheter tip from view. A quantifiable angular displacement coordinate is used to determine bend and trajectory of the catheter. This quantifiable angular displacement coordinate, as will be further described by way of FIGS. 4-8 comprises a locus of points between the first detectable marker and the second detectable marker. Each point in the locus of points is defined by a distance vector between the first detectable marker and the second detectable marker along a line that is perpendicular to the first detectable marker and extends outward to the second detectable marker. Such an arrangement defines an angular displacement coordinate and is used to determine the trajectory of the catheter of the present invention by an imaging system. At least two detectable markers are necessary, and a plurality of detectable markers allows for time dependent imaging of catheter placement and extraction.

Figure 2:
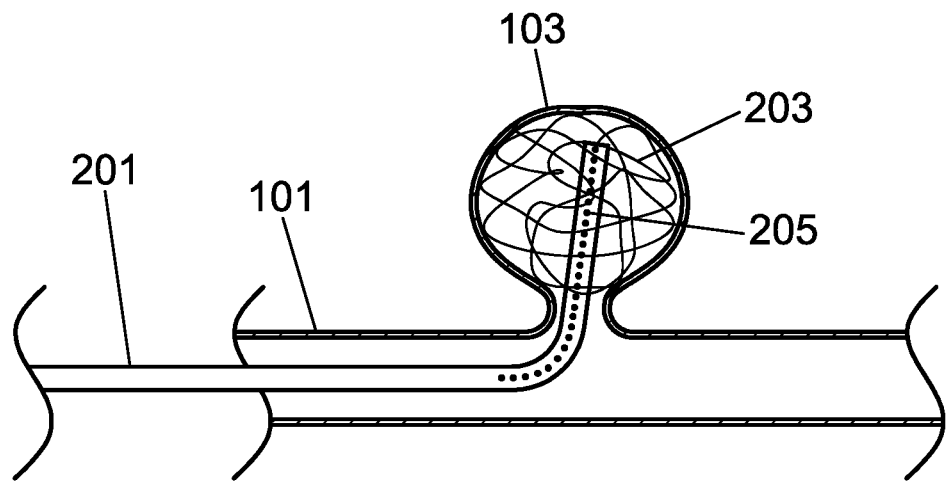
FIG. 2 depicts a second embodiment of the present invention in use.
Figure 3:
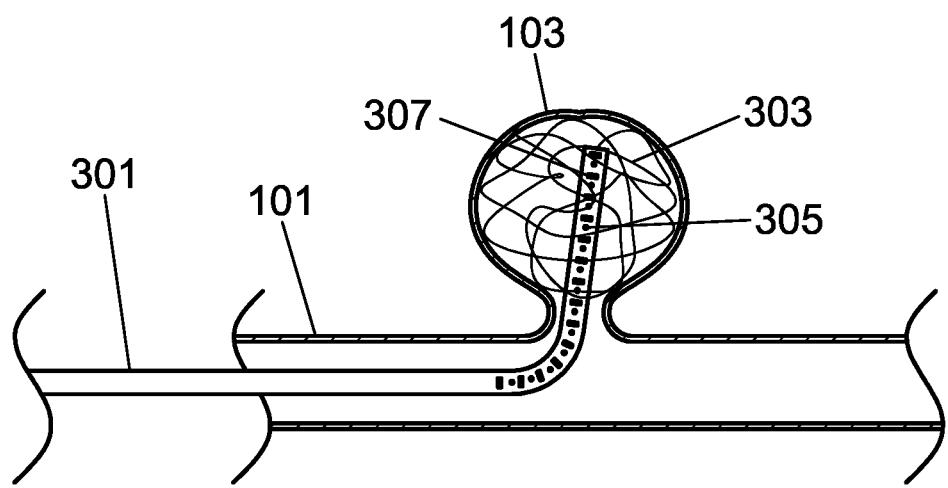
FIG. 3 depicts a third embodiment of the present invention in use.

Turning to the drawings, FIGS. 1-3 depict several embodiments of the catheter of the present invention in use placing a coil in an aneurysm. FIG. 1 depicts a vessel 101 such as an artery with an aneurysm 103 formed as a bulging, weak area in the wall of the artery 101. A minimally invasive technique to treat the aneurysm is endovascular coiling, where a soft, flexible wire known as a coil 107 is fed into the aneurysm by way of a catheter 105. The coil 107 is commonly made from a metal such as platinum. The coil 107 creates a twisted mass that fills the space within the aneurysm and causes clotting that seals off the aneurysm from the artery. During endovascular coiling, the surgeon moves the catheter 105 into the aneurysm 103 in such a way as to allow filling of the aneurysm space with the coil 107 without contacting or piercing the wall of the aneurysm, an event that could cause patient morbidity. The catheter is placed in a small incision in the groin area of a patient and under fluoroscopy the catheter is threaded through a vessel and eventually into the aneurysm. The coil 107 is then deployed through the catheter into the aneurysm 103. As the aneurysm 103 becomes filled with the coil 107, it becomes more difficult to detect the tip of the catheter under fluoroscopy due to the radiodense nature of the coil 107. The catheter 105 comprises a catheter body having a proximal end and a distal end, the distal end being placed within the aneurysm. The distal end comprises a first detectable marker 109 and a second detectable marker 111, each made of a radiodense material such as a metal, or an emitter of electromagnetic radiation such as quantum dots. There may be additional detectable markers, each of which provide a fluoroscopic representation of the tip of the catheter as well as its trajectory and the overall shape of the catheter at any moment during the procedure. FIG. 1 depicts the markers as bands or rings that are attached or otherwise adhered to the catheter in a circumferential manner. The bands or rings may be circumferential to the catheter body in whole or in part. Each band or ring being parallel to an adjacent band or ring such that when the catheter bends, the bands or rings are no longer parallel at the bend, and the angle made by the now non-parallel bands or rings can be measured by a fluoroscope or similar imaging equipment. The measurements are then processed by a computer having a processor, memory, and computer readable media to correlate the angles with the curvature of the catheter. With the introduction of the time domain, the changes in angle with respect to time can be used to determine the trajectory and expected location of the catheter and tip (distal end). FIG. 2 depicts a second embodiment of the present invention where the catheter 201 comprises a plurality of markers 205 along the length of the catheter, where the markers provide a fluoroscopic representation of the tip of the catheter as well as its trajectory and overall shape during any moment of the procedure. The markers 205 are made from a radiodense material such as a metal, or an emitter of electromagnetic radiation such as quantum dots, and provide a fluoroscopic representation of the catheter 201 and tip without being obscured by the coil 203. The markers 205 are of similar geometries and are used to provide information to the imaging system regarding catheter location. The markers comprise discrete elements spaced along an insertion/extraction axis of the catheter. Sensors may also be incorporated into the markers that emit radiation or change imaging characteristics when influenced by externalities that the sensor responds to.

FIG. 3 depicts a third embodiment of the present invention where the catheter 301 comprises a first marker 305 and a second marker 307, where the markers provide a fluoroscopic representation of the tip of the catheter, trajectory, and overall shape. The first marker 305 and the second marker 307 are made from a radiodense material such as a metal, or an emitter of electromagnetic radiation such as quantum dots, and provide a fluoroscopic representation of the catheter 301 and tip without being obscured by the coil 303. The first marker 305 and the second marker 307 are of differing geometries to provide additional information to the imaging system regarding catheter location. In some embodiments of the present invention, different marker geometries are employed to provide additional information to an imaging system and related computer system regarding catheter location during a medical procedure. This information may include, for example, a linear coordinate along the insertion/extraction axis, a distance or coordinate marker, anatomical measurement markers, and the like.

Figure 4:
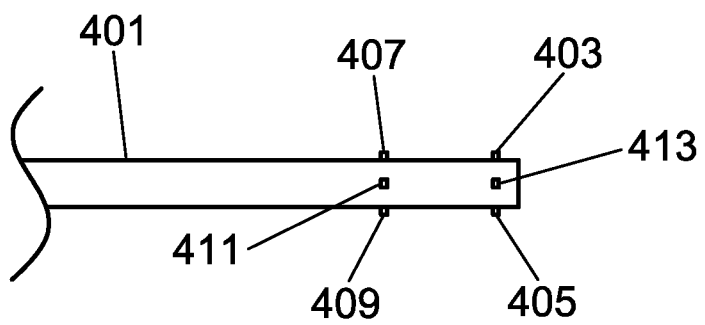
FIG. 4 is a plan view of a catheter tip according to one embodiment of the present invention.
Figure 5:
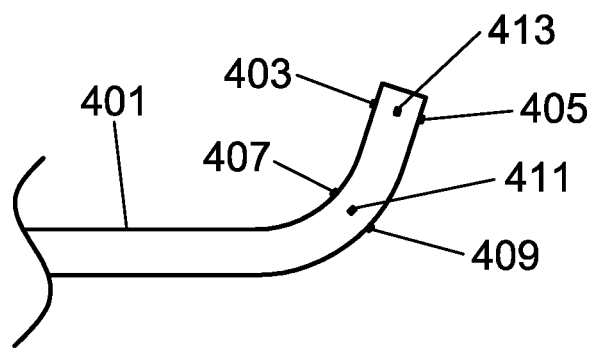
FIG. 5 is a plan view of the catheter tip of FIG. 4 in a bent position.

Determining the location of the catheter as well as its trajectory is of utmost importance in most if not all clinical procedures. While the markers employed in the present invention provide Cartesian coordinate information to a downstream imaging system, angular or polar coordinates are beneficial in providing information on the curvature of the catheter during a clinical procedure. As such, several embodiments of the present invention provide this curvature or angular information. FIGS. 4 and 5 depict a series of markers that form a parallel arrangement when the catheter 401 is straight, and a non-parallel arrangement of markers when the catheter bends. These multiple markers provide an accurate predictor of catheter tip location. In some embodiments of the present invention, uncertainty of location is provided in the downstream imaging system, as colored zones of proximity, where each color indicates a statistical probability that the catheter or the catheter tip is in fact in that location. This probability of error is therefore color coded and assigned to the resulting image direction vector and distal end location. A color overlay that provides a visual indicator of the probability that the catheter tip or portion thereof is in a certain location facilitates good surgical decision making. The color overlay may be displayed along with the resulting fluoroscopic image of the surgical procedure, and may be provided to the surgeon in real time. In FIG. 4, the catheter 401 comprises a first marker 403, a second marker 405, a third marker 407, and a fourth marker 409. More or less than four markers may be used in various embodiments of the present invention. Between the various markers are alignment markers such as the first alignment marker 413 and the second alignment marker 411 that provide, for example, additional information related to catheter placement and positioning. As can be seen in FIG. 5, as the catheter 401 is bent, the markers and alignment markers create non-parallel lines where the angles formed by these non-parallel lines can be used to predict the curvature of the catheter 401.

Figure 6:
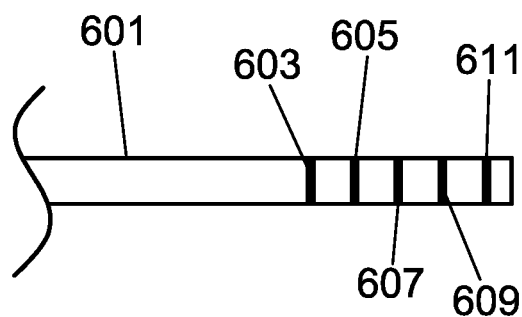
FIG. 6 is a plan view of a catheter tip according to another embodiment of the present invention.
Figure 7:
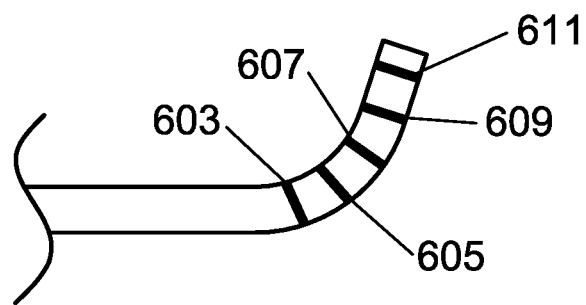
FIG. 7 is a plan view of the catheter tip of FIG. 6 in a bent position.
Figure 8:
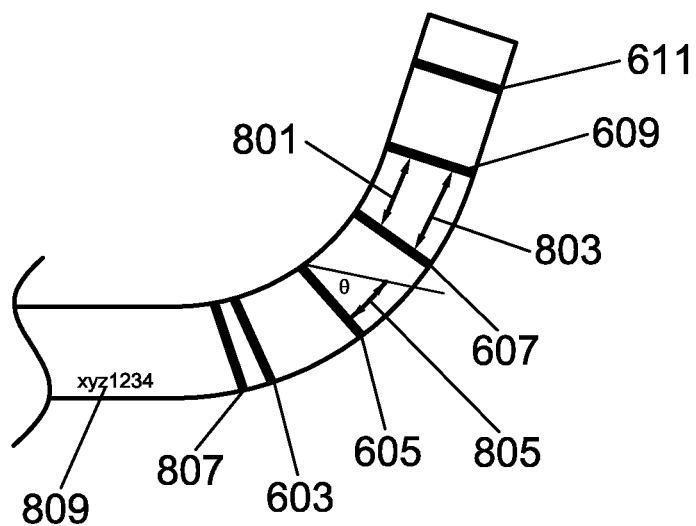
FIG. 8 depicts coordinate extrapolation of catheter tip and body.

FIGS. 6-8 depict a catheter tip with banded markers. In FIG. 6, each of the markers 603-611 comprise a band, line or ring that is orthogonal with the axis of the catheter when the catheter 601 is in a straight, unbent position. There may be more or fewer markers in various embodiments of the present invention. Each of the markers are further parallel with each other when the catheter 601 is in a straight, unbent position. As the catheter bends, as seen in FIG. 7, the markers are no longer parallel with each other. As seen in FIG. 8, the spacing between markers will vary and create an inner intermarker distance 801 and an outer intermarker distance 803. These distances can be used to determine the curvature of the catheter along the section between the two markers 607 and 609 in this example. An angular displacement coordinate 805 may also be determined by measuring the angle between a marker such as the fourth marker 605 and a given or fixed reference line. This angular displacement coordinate will also provide the curvature of the catheter at that section. The given or fixed reference line may also be an alignment marker such as the alignment marker 807 depicted in FIG. 8. The alignment marker 807 may also be used to indicate magnification in the downstream imaging system. In some embodiments of the present invention, a unique catheter identifier 809 may be etched, printed, or otherwise attached to the catheter using radiodense material. The unique catheter identifier 809 may contain information such as a serial number, physical properties of the catheter such as catheter length, diameter, materials, Young's Modulus of the catheter, and the like. The catheter identifier 809 contains catheter properties, calibration properties, etc., of which may in turn be used to practice methods of the present invention as subsequently set forth herein.

Figure 9:
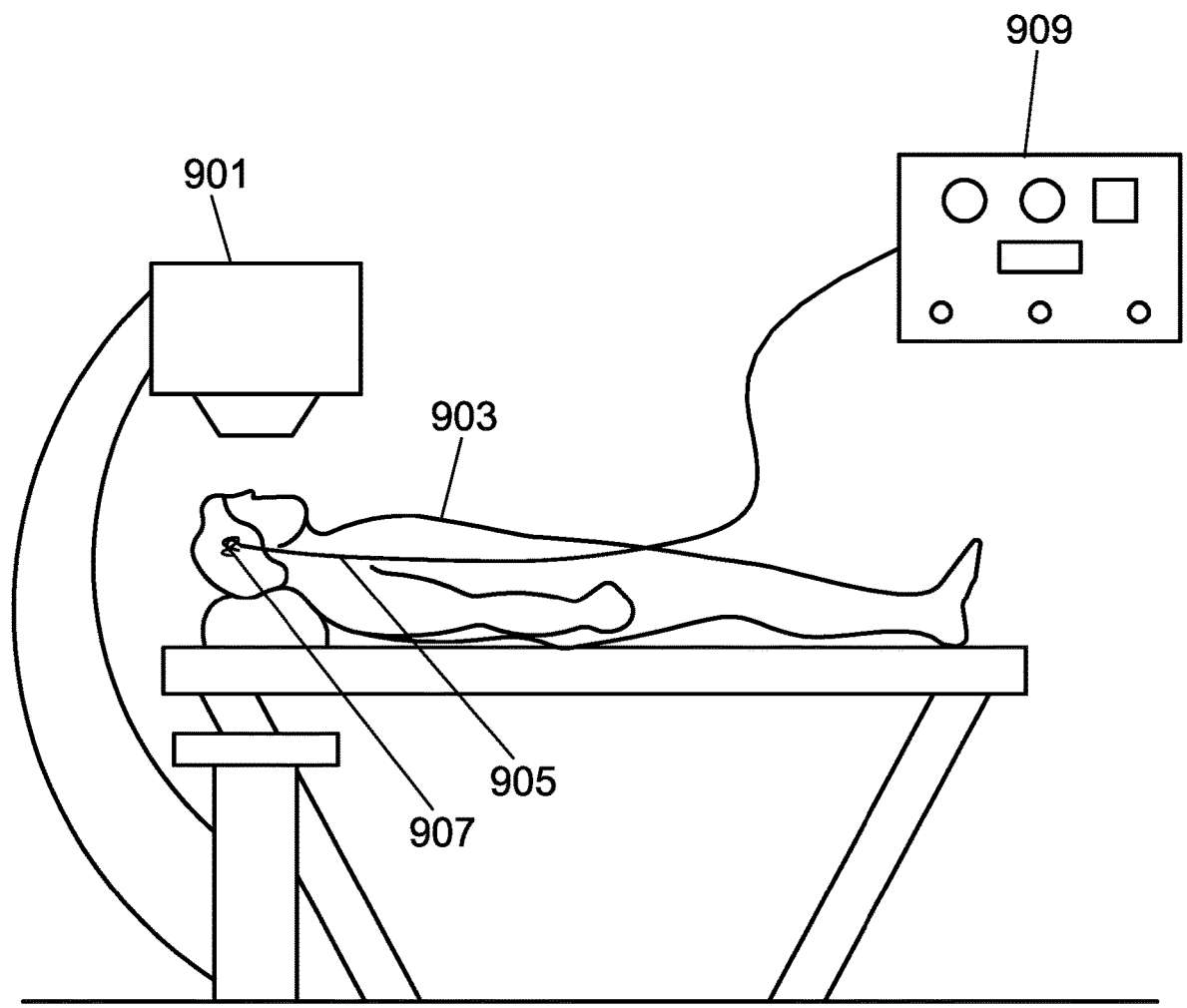
FIG. 9 shows an overall system for catheter detection, tracking, and virtual image reconstruction.

FIG. 9 shows an overall system for catheter detection, tracking, and virtual image reconstruction in use. A patient 903 can be seen in an X-ray system used for fluoroscopic procedures such as angiograms. An X-ray emitter 901 can be seen connected to angiography equipment 909. In FIG. 9, a catheter 905 is seen entering an aneurysm that is being filled by a coil 907. The catheter 905 comprises detectable markers as previously described so that the catheter tip can be visualized without blocking by the radiodense coil 907. The system comprises an X-ray emitter 901, a fluoroscope or similar angiography equipment 909 is configured to receive X-rays from the X-ray emitter 901 as the X-rays pass through the patient 903, a catheter 905 for insertion within the patient can also be seen. The catheter comprises a catheter body having a proximal end and a distal end, a plurality of detectable markers located at the distal end of the catheter body; and a plurality of quantifiable angular displacement coordinates, each angular displacement coordinate comprising a locus of points between adjacent detectable markers, where each point is defined by a distance vector between each adjacent detectable marker.

The system further may comprise a computer program executable on a computer having a processor, memory and computer readable media, and operatively coupled to the fluoroscope, the computer program configured to convert the plurality of quantifiable angular displacement coordinates into both a direction vector and a distal end location of the catheter being inserted within the patient. In such a way, the catheter trajectory can be determined and guided in real time during surgery, with critical course corrections made to prevent catheter tip placement in unwanted areas that could result in a medical emergency or patient mortality.

Figure 10:
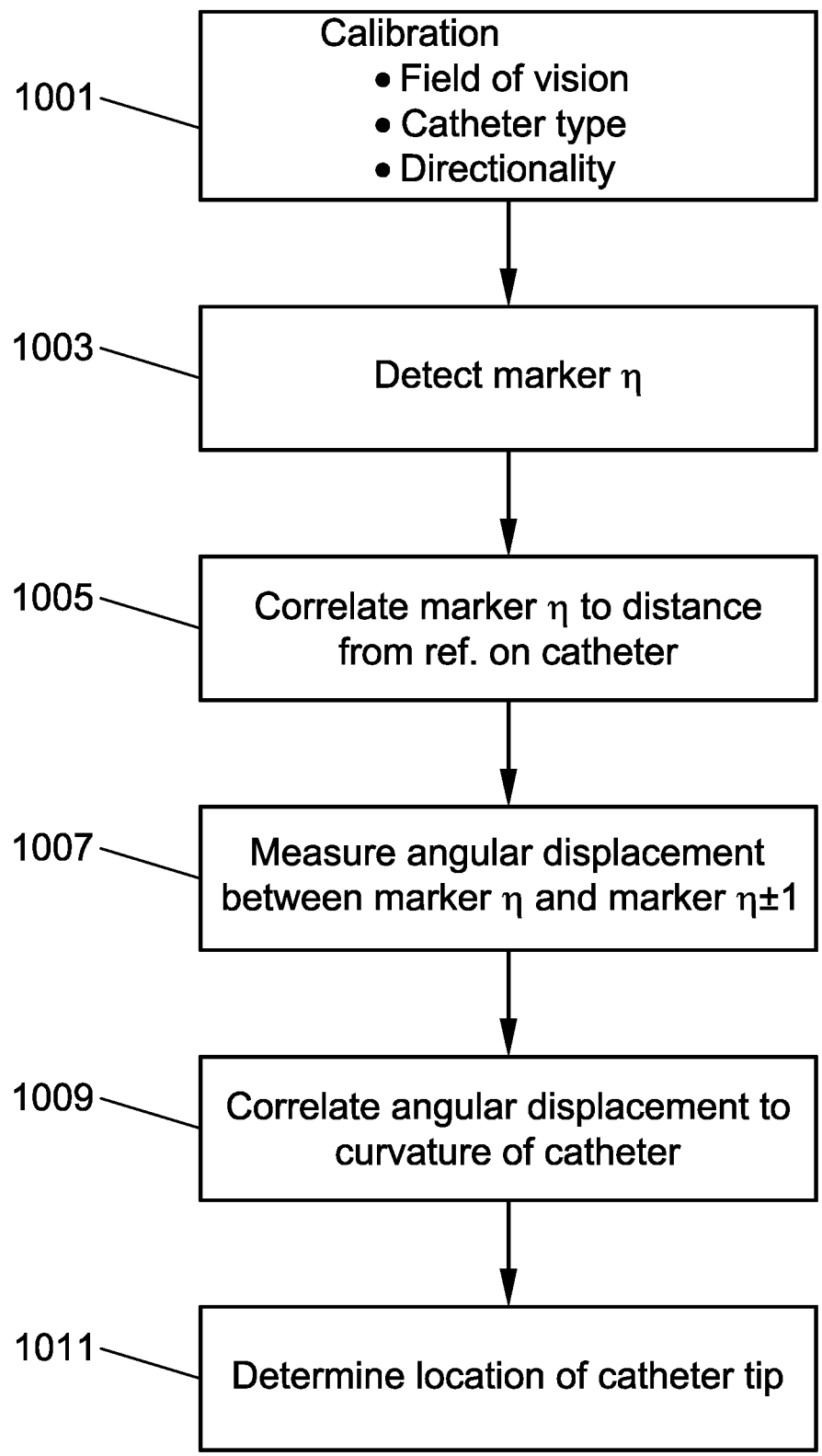
FIG. 10 is a flowchart depicting a method of virtual image reconstruction of the present invention.

FIG. 10 is a flowchart depicting a method of virtual image reconstruction of the present invention. The method described by way of FIG. 10 is computer implemented, and may, in some embodiments of the present invention, be part of the angiography equipment. In step 1001, a calibration procedure is initiated to determine the field of vision to be imaged, the directionality of the biplane or X-ray source and receiver, as well as catheter type. The catheter type may be manually input, be contained in a data file or data structure, or be read using a unique identifier such as that depicted as 809 in FIG. 8. Once calibration setup is complete, the imaging system detects the markers in step 1003. Distance measurements are made between markers or between markers and references in step 1005. To determine catheter bend and directionality, angular displacement measurements are taken, as previously described by way of FIG. 8 and the associated description thereof. These angular displacement measurements are then correlated to curvature of the catheter in step 1009 to provide the clinician with an overall image of the catheter during the procedure, and further processing of the collected measurements provides a determination of the location of the catheter tip in step 1011. Color or shading may be used in displaying the catheter on a screen to provide zones of probability for the exact location of the catheter tip or catheter body should uncertainty exist in the measurements.

The computer-based method described by way of FIG. 10 allows for determination of the location of a catheter tip during a medical procedure. The method comprises the steps of establishing on a computer having a processor, memory and computer readable media calibration parameters for a catheter visualization procedure, wherein the computer is operatively coupled to a fluoroscope; detecting with a fluoroscope a detectable marker n located at a distal end of a catheter body; measuring with the computer a distance from a reference on the catheter body to the detectable marker n; detecting with the fluoroscope a detectable marker n+1 located at the distal end of the catheter body; measuring with the computer angular displacement between detectable marker n and detectable marker n+1; correlating with the computer the measured angular displacement between detectable marker n and detectable marker n+1 to curvature of the catheter; determining the location of the tip of the catheter using the correlated curvature information and the calibration parameters; and displaying the location of the tip of the catheter on a computer display. In some embodiments of the present invention, the method further comprises the steps of assigning on the computer a probability of error for the location of the tip of the catheter, and converting the probability of error into a color overlay of the location of the tip of the catheter displayed on a computer display.

Figure 11:
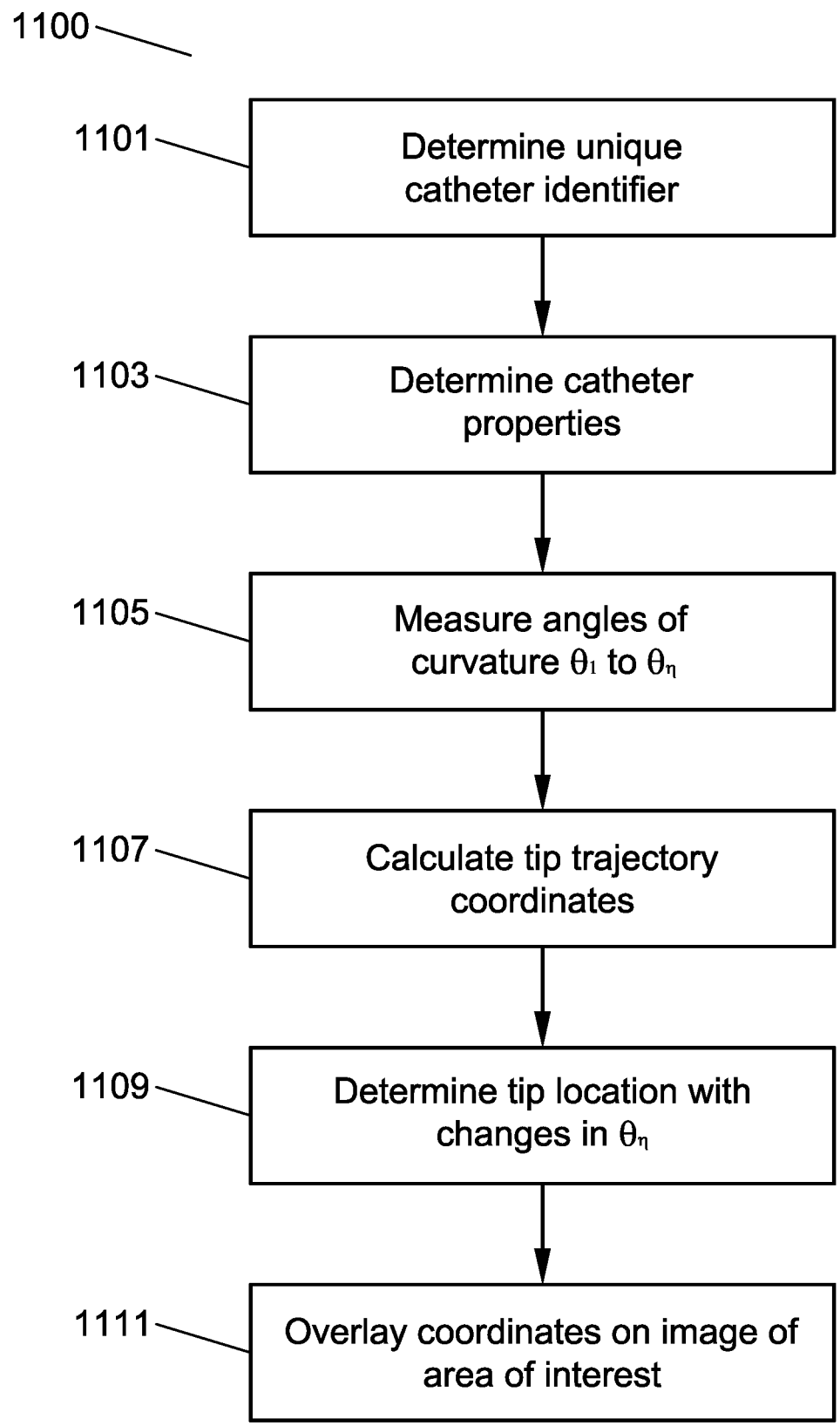
FIG. 11 is a flowchart depicting a method of determining catheter curvature and tip location of the present invention.

FIG. 11 is a flowchart depicting a method of determining catheter curvature and tip location of the present invention. The method described by way of FIG. 11 is computer implemented, and may, in some embodiments of the present invention, be part of the angiography equipment. In step 1101, identification of the catheter occurs by retrieving a unique catheter identifier using a manual process, a process coupled to a data file or data structure, or read using a unique identifier such as that depicted as 809 in FIG. 8. From the unique identifier, properties of the catheter are determined in step 1103. These properties include, for example, catheter length, catheter diameter, catheter material, Young's Modulus and elasticity of the catheter, and the like. From measurements taken of the markers, angles of curvature are determined in step 1105, as previously described herein. The angles of curvature are then used to determine catheter tip trajectory coordinates in step 1107, with changes in the angles being used to determine catheter tip location in step 1109. The coordinates of the catheter and/or the catheter tip are then overlaid on an image of the area of interest, such an image being an angiogram, X-ray, or other medical diagnostic image. These steps, and the related catheter and systems described herein, provide for imaging of a catheter tip during a procedure that would otherwise obscure the image from view due to the proximity of radiodense materials to the catheter and/or catheter tip.

A computer-based method for determining the location of a catheter tip during a medical procedure is thus described. This method comprises the steps of establishing on a computer having a processor, memory and computer readable media catheter properties for a catheter visualization procedure, wherein the computer is operatively coupled to a fluoroscope; detecting with the fluoroscope angles of curvature between detectable markers on a catheter body; calculating on the computer tip trajectory coordinates using the angles of curvature detected by the fluoroscope; determining on the computer catheter tip changes in location with changes in angles of curvature; displaying a fluoroscopic image on a computer display; and overlaying the catheter tip changes in location on the fluoroscopic image.

In some embodiments of the present invention, the angles of curvature are obtained through detecting angular displacement between the detectable markers on the catheter body.

The detection of the detectable markers and associated geometric relationships between the markers that in turn provides catheter tip (distal end) location and catheter trajectory during a medical procedure is done using a three dimensional coordinate system that relies on the use of a computer, as the level and sophistication that is required cannot be done by a human in real time without the use of a computer for processing and subsequent calculations. This coordinate system may be unit-less, or may employ Metric or English units of measure. A fourth coordinate, time, is also employed as part of the methods of the present invention described and envisioned herein.

It is, therefore, apparent that there has been provided, in accordance with the various objects of the present invention, a catheter and related imaging system for detection, tracking, and virtual image reconstruction.

While the various objects of this invention have been described in conjunction with preferred embodiments thereof, it is evident that many alternatives, modifications, and variations will be apparent to those skilled in the art. Accordingly, it is intended, to embrace all such alternatives, modifications and variations that fall within the spirit and broad scope of this specification, claims and drawings appended herein.

What is claimed is:

1. A system for detection, tracking, and virtual image reconstruction of a catheter during a fluoroscopically guided medical procedure, the system comprising:
   a catheter comprising:
      a catheter body having a proximal end and a distal end;
      a first detectable marker located at the distal end of the catheter body;
      a second detectable marker located adjacent to the first detectable marker;
      wherein the first detectable marker and the second detectable marker are parallel to each other when the catheter body is straight, and non-parallel to each other when the catheter body bends; the angle made when the first detectable marker and the second detectable marker are non-parallel being correlated to a curvature of the catheter body during the fluoroscopically guided medical procedure;
   a fluoroscope based imaging system having a processor, memory and computer readable media, the fluoroscope based imaging system configured to determine the angle made between the first detectable marker and the second detectable marker, correlate the angle made with the curvature of the catheter body at a specified time, and use the changes in the angle made with respect to time to determine the trajectory and expected location of the catheter body.

2. The system of claim 1, further comprising a at least one additional detectable marker located along the catheter body.

3. The catheter of claim 2, wherein the detectable markers comprise differing geometries to provide additional information to an imaging system regarding catheter location during a medical procedure.

4. The system of claim 1, wherein the detectable markers comprise a radiodense material to provide a fluoroscopic representation of a trajectory of the catheter during a medical procedure.

5. The system of claim 1, wherein the detectable markers provide a unique signature in the presence of X-rays to provide a fluoroscopic representation of a trajectory of the catheter during a medical procedure.

6. The catheter of claim 1, wherein the detectable markers comprise quantum dots to provide a unique signature in the presence of X-rays.

7. The system of claim 1, wherein the detectable markers comprise bands circumferential to the catheter body.

8. The catheter of claim 1, wherein the detectable markers comprise discrete elements spaced along an insertion/extraction axis of the catheter.

9. The system of claim 1, further comprising an alignment marker wherein the alignment marker is configured to be used to align the catheter during the fluoroscopically guided medical procedure.

10. The system of claim 1, further comprising a unique catheter identifier made from a fluoroscopically imageable material to provide a fluoroscopic representation of the unique catheter identifier.

\* \* \* \* \*

UNITED STATES PATENT AND TRADEMARK OFFICE
CERTIFICATE OF CORRECTION

PATENT NO. : 10,952,687 B2
APPLICATION NO. : 15/062061
DATED : March 23, 2021
INVENTOR(S) : Stone et al.

Page 1 of 1

It is certified that error appears in the above-identified patent and that said Letters Patent is hereby corrected as shown below:

In the Claims

Column 8, Line 46, Claim 2, 'further comprising a at least one' should read -further comprising at least one- Signed and Sealed this
Fifth Day of April, 2022

Drew Hirshfeld
*Performing the Functions and Duties of the
Under Secretary of Commerce for Intellectual Property and
Director of the United States Patent and Trademark Office*